United States Patent
Alexander et al.

(10) Patent No.: US 12,194,115 B2
(45) Date of Patent: Jan. 14, 2025

(54) PUTTY SYSTEM, METHOD, AND APPARATUS

(71) Applicants: Kellie Alexander, Tulsa, OK (US); James DiMarino, Ocean City, NJ (US)

(72) Inventors: Kellie Alexander, Tulsa, OK (US); James DiMarino, Ocean City, NJ (US)

(*) Notice: Subject to any disclaimer, the term of this patent is extended or adjusted under 35 U.S.C. 154(b) by 794 days.

(21) Appl. No.: 17/384,065

(22) Filed: Jul. 23, 2021

(65) Prior Publication Data
US 2022/0023156 A1   Jan. 27, 2022

Related U.S. Application Data

(60) Provisional application No. 63/055,643, filed on Jul. 23, 2020.

(51) Int. Cl.
*A61K 6/90* (2020.01)
*A61C 9/00* (2006.01)

(52) U.S. Cl.
CPC .............. *A61K 6/90* (2020.01); *A61C 9/0006* (2013.01)

(58) Field of Classification Search
CPC ...................................... A61K 6/90
See application file for complete search history.

(56) References Cited

U.S. PATENT DOCUMENTS

| 6,359,057 B1 | 3/2002 | Li |
| 6,786,722 B2 | 9/2004 | Craig et al. |
| 7,083,413 B2 | 8/2006 | Parker |
| 2014/0199653 A1 | 7/2014 | Kurthy |
| 2017/0058109 A1* | 3/2017 | Nguyen ............... C08L 3/02 |
| 2019/0016877 A1* | 1/2019 | Moskal ............... C08L 29/04 |

FOREIGN PATENT DOCUMENTS

| KR | 1020160126282 | 11/2016 |
| WO | 1993017654 | 9/1993 |

OTHER PUBLICATIONS

International Search Report and Written Opinion from Corresponding PCT Patent Application PCT/US2021/042988 Mailed Dec. 6, 2021; Korean Intellectual Property Office.

* cited by examiner

*Primary Examiner* — Michael F Pepitone
(74) *Attorney, Agent, or Firm* — Head, Johnson, Kachigian & Wilkinson, PC

(57) ABSTRACT

A blockout putty for use in creating smooth finished molds, such as for use in creating a stone, gypsum, plaster, or other type cast of an impression such as, but not limited to, dental impressions of teeth and/or gums. The putty may comprise a first stage material, diluent, and lubricant. The first stage material may comprise: 0.10 to 30% by weight non-cross-linked polar polymeric resin; 1.25 to 75% by weight filler; 0.0125 to 7% by weight thickening agent; 0 to 45% by weight humectant; and 5 to 85% by weight water. For every 30 to 60 ounces of first stage material, the putty may comprise 4 to 12 fluid ounces of the diluent and 0.5 to 2.75 fluid ounces of the lubricant. The putty may further comprise dye, scent, antibacterial/antiviral/antimicrobial inhibitors, ingredients to control odor, and/or surface disinfection technologies.

6 Claims, No Drawings

PUTTY SYSTEM, METHOD, AND APPARATUS

CROSS REFERENCE

This application is based on and claims priority to U.S. Provisional Application No. 63/055,643 filed Jul. 23, 2020.

BACKGROUND OF THE INVENTION

Field of the Invention

This invention relates generally to a putty system, apparatus, and method, and more particularly, but not by way of limitation, to blockout putty for creating smooth finished molds and preventing obstructions, undercuts, defects, voids, etc. in such molds, such as for use in creating a stone, gypsum, plaster, or other type cast of an impression such as, but not limited to, dental impressions of teeth, oral anatomy, and/or gums as well as other health care, art, sculpting, and/or hobby industries.

Description of the Related Art.

When an impression is taken whether in the hobby, healthcare, sculpting, or other industry, there are instances in which the user may want to cover or block out certain areas before pouring the modeling material. By way of example only and using the field of dentistry, when an intraoral impression is taken and is poured up in a dental office or presented to a dental laboratory, it is necessary to create a cast of the impression for various dental appliances, such as but not limited to crowns, bridges, veneers, partials, dentures, orthodontic appliances, splints, bruxism appliances, study models, snore guards, sleep apnea devices, whitening trays, mouth guards, and more. It is highly desirable to create models without excess casting material around the peripheral borders of teeth or gum tissue or in areas that create an undercut, which can damage the model upon removing the impression, and to have a smooth surface outside the borders of the intended subject of the impression. Excess casting material can pose encumbrances to the user performing work on the models, which can result in ill-fitting restorations, appliances, or devices and/or can require the patient to return for another impression.

In a typical dental office and/or laboratory environment, there are a few common practices to accomplish this. The problem with most of these practices, however, is that they are time-consuming, are costly, and/or pose additional problems of their own, including unnecessary noise, debris, cleanup, and hazards to the operators, which can increase the time required to complete the process, thereby decreasing efficiency.

For example, a user may choose to simply pour the impression without blocking outside the peripheral borders not desired in the cast mold of the impression. This method often requires the user to either work with a less than optimal cast, which could result in a less than optimal dental appliance, or trim away the excess by grinding the hardened casting material after it is set, which can be very time consuming, noisy, messy, and messy and can potentially damage the desired anatomy of the cast while also placing the operator at risk of harm due to the repeated exposure to noise, aerosol, and debris while working with rotating grinding disks or handpieces. This may ultimately compromise the finished work, which may cause the dental patient unnecessary harm due to an ill-fitting appliance or could result in a longer delivery appointment if the dental professional can adjust the appliance chairside to make it fit for the patient. Unfortunately, because the environments of dental offices and dental laboratories are by necessity extremely production-oriented, this compromise is quite common.

Another method for blocking the unnecessary elements of an impression is to mix more impression material, such as an alginate, to fill in the tongue area, areas to be blocked out, and/or border areas before casting the impression in stone or other casting material. This technique works well but adds another time-consuming step of mixing more impression material, molding around the borders, and allowing the material to set up before pouring the casting material. Additionally, the material used for blocking is often messy to mix, use, and clean up, all of which adds additional work and time to the model making process. This can easily add 6 to 8 or more minutes to the procedure as well as additional cost in material. In order to save time and costs, some users will choose to block out only the tongue of the lower impression. This is usually done by mixing a small amount of impression material, such as, but not limited to, alginate, and placing it in the tongue area and allowing it to set up. The cost of the alginate is minimal but it adds another 6 to 8 or more minutes to the process before pouring the casting material.

Some users use wax to block out and box the impression. This method, even among skilled users, it quite time consuming, adding 15 minutes or more to prepare the impression to make a cast model.

Dental professionals seek an alternative to the aforementioned so the industry has offered various materials to fill the need. One such product is a malleable, dough-like material, which can also be effectively used to prepare an impression for casting. Using this material provides faster set up time than mixing additional impression material or the waxing technique. It is faster and requires less user skill than hand crafting a wax border to block out undesired areas. The problem in this technique is that some malleable martials on the market and the unset casting material are both porous so that the dough often sticks to the cast. After the impression is pulled from the model, the dough must be picked off of the model, and a toothbrush or similar type brush is used under running water to clean the dough off the model. This can often take several minutes, thus negating any time saved and may result in damage to the desired cast anatomy due to the scrubbing and washing. Another problem with this method is that the dough-like material inhibits the stone from completely setting to a hardened state, creating a mushy layer about 0.5 to 2 mm thick between the dough-like material and the hardened stone. This results in a soft, wet, sticky surface on the cast next to where the dough was placed on the borders, which can be problematic, particularly for procedures where the borders are critical, such as partials, dentures, and other appliances. This mixture of the dough-like material and the mushy stone may impart inaccuracies into the final dental cast, which can then cause an ill-fitting dental appliance. Furthermore, the dough-like material is typically a highly liquid soluble, and thus cannot be rinsed or disinfected without dissolving into mush. In essence, it is intended for one-time use, making it costly.

Another challenge currently experienced in the dental profession occurs when a malleable material lacks sufficient support to hold an impression, device, border mold, restoration such as but not limited to a denture, etc. in the correct horizontal and vertical dimensions when it is placed in the malleable material. Typically, material may be forced laterally as the impression is placed into the material, which can result in defective, thin, and/or inadequate models, broken or ill-fitting restorations, or excess modeling material, which would require trimming.

Yet another common challenge may occur when pouring up dental impressions. Typically, a user must guess how much material to displace in advance of placing the impression into the material. If the user does not displace any material, the force of inserting the impression into the material could cause the material to exert forces onto the impression and/or the impression tray that causes the impression and/or the impression tray to be pushed or pulled in a manner that can cause distortion, which may result in an ill-fitting appliance and could lead to intra-oral patient injury, increased risk of appliance failure, and/or harm to the patient. One can envision that if the material forces the impression material to contract, the restoration which is made on the model may be smaller and not fit accurately in the mouth or require the dental professional to have to adjust the appliance, which is time consuming. Alternatively, if the material forces the impression material and/or impression tray to expand, the restoration which is made on the model may be larger and not fit accurately in the mouth. Either way, the result would be that the patient would either have an ill-fitting appliance or the patient would have to have another impression taken and the fabrication process repeated, which can take several weeks. Additionally, if the impression goes back to the same dental lab or is fabricated by the same technique, a similar result is likely the second time around.

Based on the foregoing, it is desirable to provide a putty-like material that produces superior working models without the need for additional steps to trim or clean the model.

It is further desirable for the putty material to be a reusable product that can be easily and swiftly set in place on the dental impression and/or tray, cleanly separated from the dental model, rinsed, and disinfected after use so that it may be re-used.

It is further desirable to provide a device for use with the putty to support and prevent lateral flow thereby reducing the time required to prepare the impression for modeling.

It is further desirable to provide a method of using the putty to prevent the putty from exerting force that may distort the impression.

SUMMARY OF THE INVENTION

In general, in a first aspect, the invention relates to a putty comprising a first stage material, diluent, and lubricant. The first stage material may comprise: 0.1-30% by weight non-crosslinked polar polymeric resin; 1.25-75% by weight filler; 0.0125-7% by weight thickening agent; 0-45% by weight humectant; and 5-85% by weight water. More specifically, the first stage material may comprise 0.5-15% by weight non-crosslinked polar polymeric resin; 5-50% by weight filler; 0.1-3% by weight thickening agent; 0-30% by weight humectant; and 20-70% by weight water.

The first stage material may be mixed with a variety of second stage materials to create putties with various physical properties such as but not limited to: tackiness, stickiness, firmness, flow, etc. First stage and second stage materials may be mixed to create the putty. For example, for every 30 to 60 ounces of the first stage material, the second stage materials may comprise 4 to 12 fluid ounces of diluent and 0.01 to 10 fluid ounces of lubricant. More specifically, for every 37 to 52 ounces of the first stage material, the second stage materials may comprise 6.25 to 10.125 fluid ounces of diluent and 0.5 to 2.75 fluid ounces of lubricant. More specifically, for every 42 ounces of the first stage material, the second stage materials may comprise 8 fluid ounces of diluent and 1 fluid ounce of lubricant. Alternately, every 40.5 to 41 ounces of putty may comprise 21 ounces of the base material, 7.75 to 8 ounces of diluent, and 11.75 to 12 ounces of lubricant. The second stage materials may further comprise dye, antimicrobial agents, fragrance, or other desired materials. In a second aspect, the invention relates to a method of making the putty, the method comprising: placing the first stage material, diluent, and lubricant in a container; heating the first stage material, diluent, and lubricant, and dye if used; and kneading the first stage material, diluent, and lubricant together to form the putty. As noted above, the lubricant may be vegetable oil and the diluent may be water. The first stage material, diluent, and lubricant may be placed in the container in the following ratio: for every 30 to 60 ounces of the first stage material, the second stage materials may comprise 4 to 12 fluid ounces of diluent and 0.01 to 10 fluid ounces of lubricant. More specifically, for every 37 to 52 ounces of the first stage material, the second stage materials may comprise 6.25 to 10.125 fluid ounces of diluent and 0.5 to 2.75 fluid ounces of lubricant. More specifically, for every 42 ounces of the first stage material, the second stage materials may comprise 8 fluid ounces of diluent and 1 fluid ounce of lubricant. Alternately, every 40.5 to 41 ounces of putty may comprise 21 ounces of the base material, 7.75 to 8 ounces of diluent, and 11.75 to 12 ounces of lubricant.

The method may further comprise adding dye to the first stage material, diluent, and lubricant prior to kneading, and kneading until a uniform color is established. Heating the first stage material may occur at 32-52 degrees Celsius for 5 to 40 minutes. More specifically, heating the first stage material may occur at 35 to 50 degrees Celsius for 10 to 30 minutes, or even more specifically at 42 degrees for 20 minutes. The first stage material may not be heated higher than 49 degrees Celsius. The method may further comprise allowing the putty to cool to room temperature.

In a third aspect, the invention relates to a method of producing a cast model of a dental impression, the method comprising: forming a ball out of the putty described above; placing the ball of putty over a user's fingers; inserting a tray handle of the dental impression into the putty to prevent interference of the anterior border; rolling the putty to a peripheral border of the dental impression; pouring casting material into the dental impression; allowing the casting material to set into a mold; and removing the putty from the mold.

The method may further comprise spraying the putty with disinfectant and rinsing the putty with water after removing the putty from the mold. The method may further comprise reusing the putty.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

In general, in a first aspect, the invention relates to a putty material suitable for use as a blockout putty for creating smooth finished molds, such as for use in creating a stone, gypsum, plaster, or other type cast of an impression such as, but not limited to, dental impressions of teeth and/or gums as well as other health care, arts, sculpting, and/or hobby industries. The putty may provide a precise viscosity, specific tackiness, and moldability to achieve superior modeling results in a fraction of the time. The putty may be insoluble so that it does not interfere with the setting of the casting material, thus preventing the putty from sticking to the finished cast model.

The putty may be manufactured in a single or multiple stage process. In a multiple stage process, the first stage material may comprise 0.1-30% by weight non-crosslinked polar polymeric resin; 1.25-75% by weight filler; 0.0125-7% by weight thickening agent; 0-45% by weight humectant; and 5-85% by weight water. More specifically, the first stage material may comprise 0.5-15% by weight non-crosslinked polar polymeric resin; 5-50% by weight filler; 0.1-3% by weight thickening agent; 0-30% by weight humectant; and 20-70% by weight water. In particular, the first stage material may be the modeling dough described in U.S. Pat. No. 6,359,057, which is incorporated herein by reference.

The first stage material may be mixed with a variety of second stage materials to create putties with various physical properties such as but not limited to: tackiness, stickiness, firmness, flow, etc. First stage and second stage materials may be mixed to create the putty. For example, for every 30 to 60 ounces of the first stage material, the second stage materials may comprise 4 to 12 fluid ounces of diluent and 0.01 to 10 fluid ounces of lubricant. More specifically, for every 37 to 52 ounces of the first stage material, the second stage materials may comprise 6.25 to 10.125 fluid ounces of diluent and 0.5 to 2.75 fluid ounces of lubricant. More specifically, for every 42 ounces of the first stage material, the second stage materials may comprise 8 fluid ounces of diluent and 1 fluid ounce of lubricant. Alternately, every 40.5 to 41 ounces of putty may comprise 21 ounces of the base material, 7.75 to 8 ounces of diluent, and 11.75 to 12 ounces of lubricant. The putty may comprise 45% to 55% by weight first stage material; 15% to 25% by weight diluent; and 15% to 35% by weight lubricant.

The diluent may be water or any other desired diluent, while the lubricant may be oil or any other desired lubricant. The second stage materials may further comprise dye; surfactant; emulsifier; organoleptic ingredients; antibacterial, antiviral, and/or antimicrobial inhibitors, agents, or additives; scent(s) and/or aromatic(s); ingredients to control odor; surface disinfection technologies; and/or other desired materials. The dye may be food dye, for example, or another colorant. For example, the putty may comprise red food dye, such that the finished product has a pink tint. For the quantities described above, the putty may further comprise 5 to 15 drops of dye, or more specifically 10 drops of dye, or any other desired quantity of dye.

In a single stage process, all ingredients described above for the first stage material and all additional ingredients described above as being added during the second stage may be combined in a single stage or added over multiple stages if needed.

To make the putty, the first stage material, diluent, and lubricant, as well as the dye and any other supplements if used, may be placed together in a suitable container. For example, for the quantities provided above, the ingredients may be placed in a four- to twelve-quart glass bowl or pan or other container. The container may be placed in a preheated warming oven at a low temperature, such as at 32 to 52 degrees Celsius for 10 to 30 minutes, or more specifically at 42 degrees Celsius for 20 minutes. The warmed ingredients may then be kneaded together until thoroughly blended. When dye is included, the ingredients may be adequately mixed when the putty becomes a uniform color. The putty may be cooled to room temperature before being divided into appropriate portions for use. The quantities and process described herein may be altered and/or be scaled up for varying putty consistencies and/or high-volume production.

During use with a dental impression, the user may determine the desired peripheral border of the impression. Optionally, the user may mark the desired border, such as with a pen. The user may then palm a portion of the putty to form a ball approximately 1.5" to 5" in diameter, or more specifically 2.5" in diameter, similar to the size of a tennis ball or softball. The user may place the ball of putty over the fingers of one hand. With the impression in the other hand, the user may insert the impression handle of the tray first, to bury in the putty, which may eliminate interference of the anterior border of the impression. Holding the impression, the user may begin rolling the putty to the peripheral border previously established. The putty may be easily manipulated by hand to conform around the impression securely. This may be done in a matter of seconds. Once the material is formed around the impression, blocking out the undesirable areas, the impression may then be poured in any casting material appropriate for the intent of the cast model.

If the user wishes to block out only the tongue area, this may likewise be done in a matter of seconds. The user may place an approximately 1.5" diameter ball in the area cut out on the lower impression tray to fill the area. The user may conform/form the putty to the desired border. The user may then pour the casting material.

Once the casting material is set, the user may remove the putty from the mold. The putty may leave little to no residue on the cast. The user may then spray the putty with surface disinfectant and rinse the putty in water, allowing the putty to be reused. The user may store the putty in an airtight container.

The blockout putty of the present invention may dramatically reduce the time required to prepare dental impressions for casting to about one minute and may reform the way models are made.

Alternately, the putty may be used in conjunction with a lateral flow retention device (LFRD). The LFRD may be a container made in any shape, including, but not limited to, one that mimics the desired shape of the finished model such as a circle with a flat end. The LFRD may provide support to prevent the putty from flowing laterally so that the impression may be able to be positioned in the proper horizontal and vertical orientation. The LFRD may also be designed to produce the desired model base and even impart designs, branding, lettering, messaging, etc. into the model base to further assist with model, patient, product branding, marketing, identification, or aesthetic enhancements. The LFRD may also be used to store the putty. The LFRD may be used with or without a boxing former.

During use of the system comprising the putty and the LFRD, the user may select an appropriate amount of putty or utilize a putty portion dispenser, which may be a scoop, container, or measuring device with pre-determined markings representing an appropriate amount of putty to use for various processes, such as but not limited to boxing with no LFRD, boxing with an LFRD, boxing with a form, or any other technique for which it would be helpful to pre-measure an appropriate amount of putty. The user may fill the putty portion dispenser to a desired marking as noted on the putty portion dispenser for the technique they are using. In this example, the user may use the marking for boxing with the LFRD. The user may then remove the putty from the putty portion dispenser, roll the putty on their palm to make it smooth, and form a ball. The user may place the ball of putty into the LFRD. The user may then insert the impression into the putty and proceed with casting the model.

Additionally or alternately, the putty of the present invention may be used with a troughing technique, which is the process by which a user may utilize their fingers, palm, or hand to displace an appropriate amount of putty to form a trough before the impression is placed, thereby allowing the impression to rest passively in the putty without the putty exerting any forces on the impression. Additionally, a troughing device may be used to help increase speed, efficiency, and accuracy of the size and shape of the troughs. The troughing device may displace the appropriate amount of putty based on the impression used and the desired technique, thereby reducing the learning curve, eliminating the guess work, and greatly improving accuracy and efficiency. The system may comprise multiple troughing devices of different sizes and styles. Each troughing device may be made to fit a particular type of impression or technique such as, but not limited to, mandibular dentures, maxillary dentures, mandibular partial-dentures, maxillary partial-dentures, sleep apnea devices, snore guards, and other devices. Each troughing device may be designed to displace the correct amount of putty so that the impression can easily be positioned into the putty at the proper horizontal and vertical orientations without the putty exerting any deformational forces on the impression tray and/or impression. The troughing device may be reusable or disposable. The troughing device may be made to fit a particular type of impression or technique such as, but not limited to, mandibular dentures, maxillary dentures, mandibular partial-dentures, maxillary partial-dentures, sleep apnea devices, snore guards, and other devices. The shape of the troughing device may mimic the shape of the impression taken to capture impressions for fabricating dentures, partial dentures, etc. Since the troughing device may have a similar shape to the impression tray and/or impression material and may be made of a rigid material, it may displace the putty, creating a trough into which the impression can passively rest without being subjected to the forces that could damage the impression and/or tray.

Once a trough has been created, the user may insert the impression handle of the tray into the putty so as to eliminate interference of the anterior border of the impression. Holding the impression, the user may begin rolling the putty to the peripheral border previously established, if needed, as this may have already been created by using the troughing device. The user may inspect the putty to ensure that it conforms around the impression securely, which may be done in a matter of seconds. Next, the modeling material may be mixed and poured into the impression and into the LFRD. By utilizing the LFRD and the troughing technique and/or troughing device, the user may be able to focus on efficiency and accuracy instead of trying to overcome the challenges users experience when not utilizing the LFRD and the troughing technique and/or troughing device, namely causing the impression to deform, which often results in an ill-fitting appliance and increases the chances of patient discomfort, repeating the process, and/or unnecessarily long appliance delivery chairside adjustments so the dental profession can determine if they can salvage the dental appliance.

Alternately, a magnetic form may be placed around the impression to help reduce the amount of modeling stone required, create a desired model base shape, eliminate the need for model trimming, allow for reusability or disposability, and increase efficiency and accuracy. The magnetic form may comprise a magnetic strip, which may be 1 to 3 inches tall and 10 to 20 inches long, or any other desired dimensions. The magnetic strip may be flexible, such that it may be looped and secured to itself to form a closed shape, with the magnetic strip forming sidewalls and with an open top and bottom. The magnetic strip may have markings denoting certain settings, allowing the user to adjust the length so that it fits the impression. For example, the markings may be set for mandibular dentures, maxillary dentures, mandibular partial-dentures, maxillary partial-dentures, sleep apnea devices, snore guards, and/or other devices. The user may simply set the magnetic strip to the desired setting and place it into the putty around the impression. The magnetic form may then act to hold the modeling material as it is being poured into the impression and while it hardens so that the desired model shape can be created.

The magnetic strip may naturally produce a roundish shape. Optionally, one or more removable clip devices may be used with the magnetic strip to create almost any shape desired, including, but not limited to, a circle with a flat side, an oval, a half-moon shape, a crescent moon shape, or other desired shape. The magnetic form may be designed to produce almost any desired model base and even impart designs, lettering, and/or messaging into the model base to further assist with model or patient identification or aesthetic enhancements.

An example of the many ways the magnetic form may be used in this system is as follows. The user may select putty and place it into the putty portion dispenser until the putty reaches the desired technique marking on the putty portion dispenser. The putty may be removed from the putty portion dispenser, rolled and smoothed, and placed into the LFRD. The appropriate troughing device may be selected and inserted into the putty. The impression may be placed into the trough created by the troughing device. The user may inspect around the impression to make sure the putty is adapted to the impression and may make any necessary adjustment, if needed. Next, the magnetic form may be set to the desired position based on the measured markings and may be inserted around the impression and into the putty to a depth of about ¼ to ½ inch. Next, the modeling material may be mixed and poured into the impression and into the magnetic form, which may also allow the user to use less modeling material since the magnetic form can be designed to adapt closer to the impression than if no magnetic form or LFRD was used.

The putty material may be suitable for use as a blockout putty for creating smooth finished molds, such as for use in creating a stone, gypsum, plaster, or other type cast of an impression such as, but not limited to, dental impressions of teeth and/or gums as well as other health care, arts, sculpting, and/or hobby industries. The putty may provide a precise viscosity, specific tackiness, and moldability to achieve superior modeling results in a fraction of the time. The putty may be insoluble so that it does not penetrate the casting material, preventing the putty from sticking to the finished cast model.

Whereas, the devices and methods have been described in relation to the drawings and claims, it should be understood that other and further modifications, apart from those shown or suggested herein, may be made within the spirit and scope of this invention.

What is claimed is:

1. A method of producing a cast model of a dental impression, the method comprising:
    forming a ball out of putty, the putty comprising:
        a first stage material, the first stage material comprising:
            0.10 to 30% by weight non-crosslinked polar polymeric resin;
            1.25 to 75% by weight filler;
            0.0125 to 7% by weight thickening agent;
            0 to 45% by weight humectant; and
            5 to 85% by weight water;
        diluent; and
        lubricant;
    placing the ball of putty over a user's fingers;
    inserting a tray handle of the dental impression into the putty;
    rolling the putty to a peripheral border of the dental impression;
    pouring casting material into the dental impression;
    allowing the casting material to set into a mold; and
    removing the putty from the mold.

2. The method of claim 1 further comprising disinfecting the putty.

3. The method of claim 1 further comprising reusing the putty.

4. A method of producing a cast model of a dental impression, the method comprising:
    placing putty in a container, the putty comprising:
        a first stage material, the first stage material comprising:
            0.10 to 30% by weight non-crosslinked polar polymeric resin;
            1.25 to 75% by weight filler;
            0.0125 to 7% by weight thickening agent;
            0 to 45% by weight humectant; and
            5 to 85% by weight water;
        diluent; and
        lubricant;
    pressing into the putty to displace a portion of the putty and form a trough;
    placing an impression into the trough such that the impression rests passively in the putty without exerting deformational forces;
    rolling the putty to a peripheral border of the impression;
    pouring casting material into the dental impression;
    allowing the casting material to set into a mold; and
    removing the putty from the mold.

5. The method of claim 4 further comprising disinfecting the putty.

6. The method of claim 4 further comprising reusing the putty.

* * * * *